(12) United States Patent
Kinlen et al.

(10) Patent No.: US 7,993,495 B2
(45) Date of Patent: Aug. 9, 2011

(54) SIGNAL ACTIVATED DECONTAMINATING COATING

(75) Inventors: Patrick J. Kinlen, Fenton, MO (US); Yiwei Ding, Ballwin, MO (US); James K. Bashkin, University City, MO (US); Shifeng Hou, Springfield, MO (US)

(73) Assignee: Crosslink Polymer Research, a division of Lumimove, Inc., St. Louis, MO (US)

( * ) Notice: Subject to any disclaimer, the term of this patent is extended or adjusted under 35 U.S.C. 154(b) by 630 days.

(21) Appl. No.: 11/471,877

(22) Filed: Jun. 21, 2006

(65) Prior Publication Data

US 2007/0114121 A1 May 24, 2007

Related U.S. Application Data

(60) Provisional application No. 60/692,529, filed on Jun. 21, 2005.

(51) Int. Cl.
- *C01B 15/01* (2006.01)
- *C01B 15/00* (2006.01)
- *A62D 3/38* (2007.01)

(52) U.S. Cl. .......... 204/175; 423/582; 588/320
(58) Field of Classification Search .......... None
See application file for complete search history.

(56) References Cited

U.S. PATENT DOCUMENTS

| | | | |
|---|---|---|---|
| 4,610,905 A | 9/1986 | von Blücher et al. | 428/90 |
| H233 H | 3/1987 | Seiders et al. | 422/1 |
| 4,677,019 A | 6/1987 | von Blücher | 428/244 |
| 4,970,145 A | 11/1990 | Bennetto et al. | |
| 5,082,550 A | 1/1992 | Rishpon et al. | |
| 5,227,042 A | 7/1993 | Zawodzinski et al. | |
| 5,518,624 A | 5/1996 | Filson et al. | |
| 5,689,038 A | 11/1997 | Bartram et al. | 588/200 |
| 5,707,915 A | 1/1998 | Taoda | 502/159 |
| 5,847,120 A | 12/1998 | Collins et al. | 540/460 |
| 5,990,373 A | 11/1999 | Klabunde | 588/200 |
| 6,011,152 A | 1/2000 | Gordon-Wylie et al. | 540/474 |
| 6,051,704 A | 4/2000 | Gordon-Wylie et al. | 540/465 |
| 6,054,580 A | 4/2000 | Collins et al. | 540/460 |

(Continued)

FOREIGN PATENT DOCUMENTS

EP 0339371 A2 11/1989

(Continued)

OTHER PUBLICATIONS

Ghosh, Anindya et al. "Green Chemistry. Sustaining a high technology civilizaton". Pure Appl. Chem., vol. 73, No. 1, pp. 113-118, 2001.*

(Continued)

*Primary Examiner* — Melvin C Mayes
*Assistant Examiner* — Sheng H Davis
(74) *Attorney, Agent, or Firm* — Nelson Mullins Riley & Scarborough, LLP

(57) ABSTRACT

A method is provided for decontaminating a surface that is susceptible to contamination by a contaminant by applying to the surface a coating which produces a decontaminating agent for the contaminant in response to a signal, connecting the electroactive coating to a source of a signal, and when the surface is contaminated, applying the signal to the electroactive coating, thereby producing one or more decontaminating agents which neutralize or destroy the contaminant. Coatings for practicing the method and articles that have been protected by the novel coatings are also provided.

13 Claims, 9 Drawing Sheets

U.S. PATENT DOCUMENTS

| | | | |
|---|---|---|---|
| 6,056,796 A | 5/2000 | Chiang et al. | |
| 6,057,488 A | 5/2000 | Koper et al. | 588/200 |
| 6,100,394 A | 8/2000 | Collins et al. | 540/467 |
| 6,235,351 B1 | 5/2001 | DiMarzio et al. | 427/453 |
| 6,316,015 B1 | 11/2001 | Rondelez et al. | 424/409 |
| 6,343,425 B1 | 2/2002 | Sias et al. | 34/389 |
| 6,387,858 B1 | 5/2002 | Shah et al. | 510/161 |
| 6,455,751 B1 | 9/2002 | Hoffman et al. | 588/200 |
| 6,525,237 B1 | 2/2003 | Purdon et al. | 588/200 |
| 6,566,574 B1 | 5/2003 | Tadros et al. | 588/200 |
| 6,569,353 B1 | 5/2003 | Giletto et al. | 252/186.28 |
| 6,692,694 B1 | 2/2004 | Curry et al. | 422/28 |
| 2001/0031243 A1 | 10/2001 | Unger | |
| 2003/0073005 A1 | 4/2003 | Kim et al. | |
| 2004/0071612 A1 | 4/2004 | Colby et al. | |
| 2004/0076543 A1 | 4/2004 | Sokolowski et al. | |
| 2004/0109853 A1 | 6/2004 | McDaniel | |
| 2004/0120844 A1 | 6/2004 | Tribelsky et al. | |
| 2004/0134857 A1* | 7/2004 | Huling et al. | 210/668 |
| 2004/0224145 A1 | 11/2004 | Weir et al. | |
| 2004/0267169 A1* | 12/2004 | Sun et al. | 601/15 |
| 2005/0010161 A1 | 1/2005 | Sun et al. | |
| 2005/0034978 A1 | 2/2005 | Kazi et al. | |
| 2005/0215871 A1* | 9/2005 | Feldman et al. | 600/309 |
| 2005/0263182 A1 | 12/2005 | Morooka et al. | |
| 2006/0072182 A1 | 4/2006 | Oh et al. | |
| 2006/0191686 A1* | 8/2006 | Blauch et al. | 166/300 |
| 2007/0278109 A1 | 12/2007 | Kendig et al. | |
| 2009/0191357 A1 | 7/2009 | Moore et al. | |

FOREIGN PATENT DOCUMENTS

| | | | |
|---|---|---|---|
| EP | WO 0200267 A1 | 1/2002 | |
| FR | 2548167 A1 | 1/1985 | |
| JP | 09-094580 | 4/1997 | |
| JP | 2002-035772 | 2/2002 | |
| WO | 9011120 A1 | 10/1990 | |
| WO | WO 02 00267 | * | 1/2002 |
| WO | WO 2004/099754 A2 | 11/2004 | |
| WO | 2008018856 A1 | 2/2008 | |

OTHER PUBLICATIONS

Collins, Terrence. "TAML Oxidant Activators: A New Approach to the Activation of Hydrogen Peroxide for Environmentally Significant Problems". Acc. Chem. Res. 35, 782-790 (2002).*

"A2C2" at www.a2c2.com/articles/lifejan02 (Jun. 16, 2006).

Gupta, S.S. et al., Science, 296:326-328 (2002) and supplementary material for article found at www.science.mag.org.

Ghosh A. et al., Pure Appl. Chem., 73(1):113-118 (201).

Collins, T.J., et al., Abstr. of Papers, 228$^{th}$ ACS National Mtg., Philadelphia, PA USA, Aug. 22-26, 2004, American Chemical Society, Washington, D.C. (2004).

Collins, T.J., et al., Abstr. of Papers, "Total degradation of organophosphorus compounds using Fe-TAML—activators of peroxide.", 226$^{th}$ ACS National Mtg., New York, NY, USA, Sep. 7-11, 2003, American Chemical Society, Washington, D.C. (2003).

Collins, T.J., et al., Abstr. of Papers, "Deactivation of bacterial spores using TAML—peroxide technology towards developing an efficient process for water disinfection.", 226$^{th}$ ACS National Mtg., New York, NY, USA, Sep. 7-11, 2003, American Chemical Society, Washington, D.C. (2003).

Banerjee, D., et al., Abstr. 35$^{th}$ Central Regional Mtg. of the Am. Chem. Soc., Pittsburgh, PA, USA, Oct. 19-22, 2003, American Chemical Society, Washington, D.C. (2003).

Gupta, S.S., et al., Book of Abstracts, 217$^{th}$ ACS National Meeting Anaheim, CA, Mar. 21-25, 1999, Am. Chem. Soc., Washington, D.C. (1999).

Gaffar, A., et al., "3810 Effects of an Activated Peroxide System on Whitening of Teeth", Abstract, Mar. 13, 2004 Hawaii Convention Center Exhibit Hall 1-2, http://iadr.confex.com/iadr/2004Hawaii/techprogram/abstract_ 40340.htm (Jun. 16, 2005).

Lim, Sang-Hoon, et al., "Bleaching of cotton with activated peroxide systems", Abstract, Coloration Technology, 2005, vol. 121, No. 2, pp. 89-95(7), Society of Dyers and Colourists, http://www.ingentaconnect.com/content/sdc/ct/2005/00000121/00000002/art00008 (Jun. 16, 2005).

Harvey, Dr. Keron, University of Liverpool—Research Intelligence—Issue No. 17—New role for fuel cells, Aug. 2003, http://www.liv.ac.uk/researchintelligence/issue17/fuelcells.html (Jun. 9, 2005).

Buckley, Dr. Leonard, "Self Decontaminating Surfaces", DARPA Defense Sciences Office, http://www.darpa.mil/dso/thrust/biosci/selfdecon.htm (Jan. 6, 2005).

Sun, Gang, et al., NTC Project C02-CD06, The Chemistry of Functional Finishing: Self-decontaminating Textile Materials, http://trc.ucdavis.edu/textiles/ntc%20projects/C02-CD06.html (Jan. 6, 2005).

Isotron supports a team of scientists and product development experts that are leaders in the area of new reactive polymers, coatings and fabrics. http://www.isotron.net/products.htm (Jan. 6, 2005).

Wander, Joseph D., Abstract, Terrorism: Chemical, Biological and Radiological Warfare, Self-Decontaminating Materials, Nov. 1, 2001, Storming Media, http://www.stormingmedia.us/14/1402/A140204.html. (Jan. 6, 2005).

Sun, Gang, et al., The Chemistry of Functional Finishing: Self-decontaminating Textile Materials, NTC Project C02-CD06 (formerly C02-E06), National Textile Center Annual Report: Nov. 2002 URL: http://trc.ucdavis.edu/textiles/ntc%20projects/gsun_ntc_2.html.

Collins, Terry, TAML® Oxidant Activators: General Activation of Hydrogen Peroxide for Green Chemistry, 1999 Presidential Green Chemistry Challenge Academic Award, Department of Chemistry, Carnegie Mellon University, Carnegie Mellon Institute for Green Oxidation Chemistry—Awards—Green Chemistry, http://www.chem.cmu.edu/groups/collins/awardpatput/award/award-gcc.html (Jun. 16, 2005).

Collins, Terrance J., TAML™ Oxidant Activators: General Activation of Hydrogen Peroxide for Green Oxidation Technologies, 1999 Academic Award, Presidential Green Chemistry Challenge, U.S. Environmental Protection Agency (EPA), Green Chemistry, http://www.epa.gov/cgi-bin/ebaprintonly.cgi (Jun. 16, 2005).

Sljukic, B. et al., Journal of the Iranian Chemical Society, (2): 1-25 (2005).

Banks, C.E. et al., Journal of the Iranian Chemical Society, (2): 60-64 (2005).

Qiang, Z., et al., Water Research, (36): 85-94 (2002).

Pletcher, D.; Electrosynethesis, (1): 4 (1999).

Duvall, S. H. and McCreery, R. L., J. Am. Chem. Soc., (122): 6759-6764 (2000).

DuVall, ja000227u Supporting Info, © American Chemical Society, J. Am., Chem. Soc., 18 pages, (2000).

International Search Report and Written Opinion for PCT/US06/24091, Jun. 21, 2006, Completed Aug. 22, 2008, mailed Sep. 8, 2008.

US 2005/0112810 A1, Kobayashi, Hironori, May 25, 2005.

Khetan, S., et al., New General Purpose Decontamination System for Chemical and Biological Warfare and Terrorism Agents, DTIC ADA451766, Nov. 20, 2003.

U.S. Patent and Trademark Office Final Office Action mailed Apr. 5, 2010, U.S. Appl. No. 12/215,357, filed Jun. 26, 2008, Shifeng Hou et al.

Patent Cooperation Treaty, International Search Report and Written Opinion, completed Oct. 19, 2009 and mailed Mar. 23, 2010, PCT Patent Application No. PCT/US09/044778, filed May 21, 2009, Lumimove, Inc., a Missouri Corporation, dba Crosslink.

K. Ho et al., Indirect catalytic epoxidation with hydrogen peroxide electrogenerated in ionic liquids, Tetrahedron, vol. 62, May 22, 2006, pp. 6650-6658, XP002550798.

U.S. Patent and Trademark Office Non-Final Office Action mailed Nov. 13, 2009, U.S. Appl. No. 12/215,348, filed Jun. 26, 2008, Von Howard Ebron et al.

A. Chagnes et al., "Thermal analysis of gamm buityrolactone and 1 butyl 3 methy imidazolium ionic liquids mixtures", Solid State Ionics 176 (2005) 1419-1427.

Jakub Reiter et al., "Ternary Polymer Electrolytes with 1-methylimidazole based Ionic Liquids and aprotic solvents", Electrochimica Acta 52 (2006) 1398-1408.

Response filed Jan. 20, 2010 with the U.S. Patent and Trademark Office to the outstanding Non-Final Office Action mailed Oct. 2, 2009, U.S. Appl. No. 12,215,357, filed Jun. 26, 2008, Shifeng Hou, et al.

U.S. Patent and Trademark Office Non-Final Office Action mailed Oct. 2, 2009, U.S. Appl. No. 12/215,357, filed Jun. 26, 2008, Shifeng Hou, et al.

PCT Cooperation Treaty, The International Bureau of WIPO, Notification Concerning Transmittal of International Preliminary Report on Patentability (PCT/IB/326) mailed Dec. 2, 2010, International Preliminary Report on Patentability (PCT/IB/373), report issued Nov. 23, 2010, Written Opinion of the International Search Authority, European Patent Office, (PCT/ISA/237, International Application No. PCT/US09/044778, filed May 21, 2009, Lumimove, Inc., A Missouri Corporation, DBA Crosslink et al.

United States Patent and Trademark Office, Non-Final Office Action mailed Sep. 27, 2010, U.S. Appl. No. 12/215,359, filed Jun. 26, 2008, Shifeng Hou et al.

Japanese Patent Office, Non-Final Official Action, issued Apr. 1, 2011, Japanese Patent Application No. 2008-529018, Lumimove, Inc. d/b/a Crosslink Polymer Research.

English translation of Patent Abstracts of Japan for Japanese Publication No. 09-094580, published Apr. 8, 1997, Japanese Patent Application No. 07-254063, filed Sep. 29, 1995, Applicant Noritsu Koki Co Ltd, Inventor Yamamoto Ken.

English translation of Patent Abstracts of Japan for Japanese Publication No. 2002-035772, published Feb. 5, 2002, Japanese Patent Application No. 2000-261894, filed Jul. 26, 2000, Applicant Ueda Seni Kagaku Shinkokai, Shirai Hiroyoshi, Inventor Shirai Hiroyoshi, Kimura Mutsumi, Hanabusa Kenji, Hamada Kunihiro, Hirai Toshihiro.

* cited by examiner

Using mediator to catalyze the reduction of $O_2$ to generate $H_2O_2$

Pt/C electrode

SIGNAL ACTIVATED DECONTAMINATING COATING

CROSS-REFERENCES TO RELATED PATENTS AND PATENT APPLICATIONS

This application is a non-provisional application of and claims priority to U.S. Provisional Patent Application No. 60/692,529, filed Jun. 21, 2005, which is incorporated by reference herein in its entirety.

GOVERNMENT LICENSE RIGHTS

This invention was made with Government support under Contract No. W911QY-06-C-0065 awarded by U.S. Army RDECOM Acquisition Center, Natick Contracting Division, Natick, Mass. The government has certain rights in the invention.

BACKGROUND OF THE INVENTION (1) Field of the Invention

The present invention relates to decontaminating coatings, and more particularly to decontaminating coatings in which the decontaminating effect is triggered by the application of a signal to the coating.

(2) Description of the Related Art

The need to protect or cleanse surfaces of contaminants is important in many different contexts. It is well known that equipment, floors, walls, counters, and the like, in hospitals and health care facilities must be sanitized regularly. Food service equipment and facilities must be cleaned and sanitized. Certain processing equipment in some manufacturing and/or diagnostic facilities demands a high level of cleanliness and freedom from contaminants.

In a different context, it is important to be able to decontaminate or neutralize chemical and biological warfare agents in order to reduce or avoid grave injury or death of human beings. In this context, the purposeful deployment of extremely aggressive and harmful chemical or biological agents is meant to cause massive contamination of exposed surfaces, which can remain dangerous to living subjects for as long as the harmful agent retains its potency and remains on the surface. Not only are organizations such as the armed forces interested in dealing with such harmful agents, but organizations such as post offices, package delivery services, and the like, are also involved.

Many sanitization and cleaning methods and compounds are well known in the art that meet the needs of common cleaning and sanitizing requirements. More recently, greater attention has been placed on improved and different techniques and compounds that can be used for the decontamination of surfaces and articles contaminated with chemical and biological warfare agents.

In U.S. Pat. No. 6,316,015, Rondelez et al., describe hyperbactericidal surfaces that are formed by binding antibiotic, bactericidal, viricidal or fungicidal molecules to the surface via a linker or spacer molecule.

In U.S. Pat. No. 6,343,425, Sias et al. describe the application of hydrogen peroxide that is activated by an electronic plasma containing $2H^+$ and $2e^-$ for the cleaning and sterilization of articles having particulates adhered thereto. Further information about this method was found under the title "A2C2" at www.a2c2.com/articles/lifejan02 (Jun. 16, 2005).

Hoffman et al., in U.S. Pat. No. 6,455,751, describe oxidizer gels for detoxification of chemical and biological agents. The gels contain oxidizing agents and thickening or gelling agents and are applied directly to a contaminated area. The high viscosity of the gel allows it to remain on tilted or contoured surfaces without flowing off. After decontamination, the residue can be washed away.

In U.S. Pat. No. 6,525,237, Purdon et al. describe a broad spectrum decontamination formulation that contains an active decontamination agent, a co-solvent, a buffer system, and a surfactant. The formulation can be dispensed as a foam onto contaminated surfaces.

Formulations for neutralization of chemical and biological toxants are also described by Tadros et al. in U.S. Pat. No. 6,566,574. The formulations can be applied as foams to contaminated surfaces and contain at least two solubilizing compounds and at least one reactive compound, which neutralize the toxant.

In U.S. Pat. No. 6,692,694, Curry et al. describe a process that involves spraying a contaminated surface with a formulation that includes an aerosol photosensitizer and then illuminating the surface, preferably with UV light, to cause the photodecomposition of chemical or biological contaminants.

Examples of more recent work include methods that involve spraying contaminated areas with a cloud of a material containing a photocatalytic oxidizing substance and then shining a high intensity beam of light of a certain wavelength that triggers a catalyzed activation that releases free radicals of the oxidizing substance (U.S. Patent Application Publ. 20040120844 A1). U.S. Patent Application Publ. 20040076543 A1 discusses a decontamination system in which a high electrical field applied across the electrodes of reactor cores causes the decomposition of contaminants that are passed through the gap region between the electrodes. Biological active coatings are discussed in U.S. Patent Application Publ. 20040109853, wherein the coatings comprise a biomolecule composition that includes a phosphoric triester hydrolase, which breaks down organophosphorous compounds of the type used in chemical warfare agents. Self-cleaning, self-decontaminating coatings are also discussed in U.S. Patent Application Publ. 2004/0224145 AI. In this coating, a transition metal oxide, such as the anatase form of $TiO_2$, is used to photochemically catalyze the formation of hydroxyl radicals by activation with UV radiation. The hydroxyl radicals cleanse the surface and degrade contaminants on the surface of the coating.

Recent work by Collins and others has been reported in which the activation of hydrogen peroxide yields an activated hydrogen peroxide species that is capable of the total destruction of certain harmful chlorophenols. See, e.g., Gupta, S. S. et al., *Science*, 296:326-328 (2002), and supplementary material for that article found at www.sciencemag.org, and Ghosh A. et al., *Pure Appl. Chem.*, 73(1):113-118 (2001). In the system described by these workers, certain homogenous amide-containing macrocyclic compounds, such as tetraamidomacrocyclic ligand (TAML®) iron catalysts, are contacted with hydrogen peroxide at ambient conditions of temperature and pressure to form activated hydrogen peroxide species that destroy contaminants such as pentachlorophenol and 2,4,6-trichlorophenol in minutes. The TAML® catalysts are described as being stable to exposure to hydrogen peroxide and as functioning in ppm (parts per million) concentrations in water to activate hydrogen peroxide to perform a broad array of oxidation reactions and some hydrolysis and/or perhydrolysis reactions. Further information on the synthesis and structures of such TAML® catalysts is found in U.S. Pat. Nos. 5,847,120 and 6,054,580. TAML® is a registered trademark of Carnegie Mellon University, Pittsburgh Pa.

This group has also reported the application of this same system for the oxidative destruction of alkyl sulfides and disulfides (Collins, T. J. et al., *Abstr. of Papers*, 228th *ACS National Mtg.*, Philadelphia, Pa. USA, Aug. 22-26, 2004, American Chemical Society, Washington, D.C. (2004)), for the degradation of organophosphorous compounds (Collins, T. J. et al., *Abstr. of Papers*, 226th *ACS National Mtg.*, New York, N.Y., USA, Sep. 7-11, 2003, American Chemical Society, Washington, D.C. (2003)), for the deactivation of bacterial spores as surrogates for biological warfare agents (Banerjee, D. et al., *Abstr.* 35th *Central Regional Mtg. of the Am. Chem. Soc.*, Pittsburgh, Pa., USA, Oct. 19-22, 2003, American Chemical Society, Washington, D.C. (2003)), and for the bleaching of azo dyes (Gupta, S. S. et al., *Book of Abstracts*, 217th *ACS National Meeting*, Anaheim, Calif., Mar. 21-25, 1999, Am. Chem. Soc., Washington D.C. (1999).

Despite the significant advances that have been made in surface decontamination technology in recent years, there remain a number of limitations in the application of available methods. For example, many of the present systems require application after a contaminating event. If the event is a significant chemical or biological warfare event, persons applying the decontamination remedy are themselves put at risk. It would be useful, therefore, to provide a decontamination system that could be put in place before a contaminating event occurs. It would be even more useful if such a system could be activated either in anticipation of an imminent contaminating event, or at any time after such an event had occurred. Moreover, it would be useful if such a system did not itself present a danger to humans or animals, such as a cloud of corrosive or toxic material, or a liquid or gel that made coated surfaces harmful to touch. It would also be useful if such a method could be activated when desired and, after the contamination danger had passed, could be deactivated and would return to a state that was harmless to humans and animals. It would be even more useful if a system that facilitated such a method could easily be returned to a state of readiness for use after an initial use. Furthermore, it would be useful if the method and the system was durable, in other words, would persist and not be leached out or washed off of protected surfaces by rain, fog, snow, or other normal environmental events. It would also be useful it such a method or system could be applied to almost any type of surface, for example to flexible materials, such as fabrics as well as to hard surfaces, such as vehicles, counter tops, walls, floors, and the like.

SUMMARY OF THE INVENTION

Briefly, therefore the present invention is directed to a novel method of producing activated peroxides in a coating, the method comprises providing a coating comprising a peroxide source and a peroxide activating catalyst; causing the peroxide source to produce a peroxide; and contacting the peroxide with the catalyst to produce activated peroxide.

The present invention is also directed to a novel method of decontaminating a surface that is susceptible to contamination with a contaminant, the method comprising: applying to the surface a coating which produces a decontaminating agent for the contaminant when an electrical potential is applied to the coating; connecting the electroactive coating to a source of an electrical potential; and when the surface is contaminated, applying an electrical potential to the electroactive coating, thereby producing the decontaminating agent and destroying the contaminant.

The present invention is also directed to a novel coating for a surface, wherein the coating comprises a peroxide source and a peroxide activating catalyst in a durable matrix.

The present invention is also directed to a novel electroactivated decontaminating coating comprising a coating which produces a decontaminating agent for a contaminant that is in contact with the coating, where the decontaminating agent is produced when an electrical potential is applied to the coating.

The present invention is also directed to a novel method of making an electroactivated decontaminating coating for a surface that is susceptible to contamination with a contaminant, the method comprising: applying at least one positive electrode and at least one negative electrode to the surface; and applying a layer comprising a matrix that is electrically conductive or ionically conductive over the positive electrode and the negative electrode, wherein the matrix contains a peroxide activating catalyst and is permeable to oxygen, water vapor, and hydrogen peroxide.

The present invention is also directed to a novel article that is coated with any one of the coatings that are described above. The present invention is also directed to a novel sensor-activated decontaminating coating system comprising: any one of the electroactivated decontaminating coatings described herein; a source of an electrical potential; electrode leads interconnecting the source of an electrical potential and the electrodes of the coating; a switch that is located in an electrical lead and which controls the application of an electrical potential to the coating; and a sensor that controls the operation of the switch.

Among the several advantages found to be achieved by the present invention, therefore, may be noted the provision of decontamination system that could be put in place before a contaminating event occurs, the provision of such a system that can be activated either in anticipation of an imminent contaminating event, or at any time after such an event had occurred, the provision of such a system that does not itself present a danger to humans or animals, the provision of such a method that can be activated when desired and, after the contamination danger had passed, can be deactivated and returns to a state that is harmless to humans and animals, the provision of such a method that can easily be returned to a state of readiness for use after an initial use, the provision of such a method and system that are durable and will not be leached out or washed off of protected surfaces by rain, fog, snow, or other normal environmental events, and the provision of such a method or system that can be applied to almost any type of substrate.

DETAILED DESCRIPTION OF THE PREFERRED EMBODIMENTS

Figure 1:
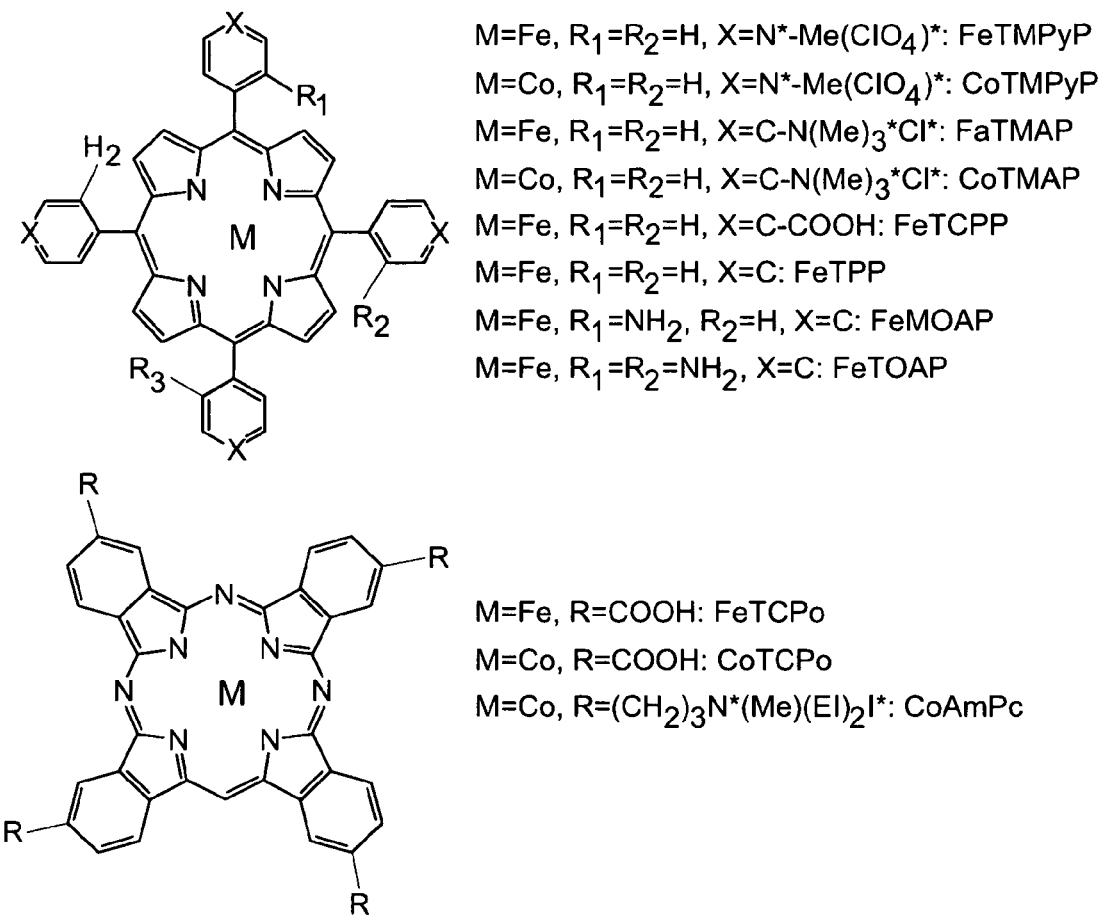
FIG. 1 shows examples of substituted porphyrins and phthalocyanines that are useful as the peroxide activating catalyst of an embodiment of the present method.

In accordance with the present invention, it has been discovered that contaminated surfaces can be decontaminated by the use of a surface coating that produces a decontaminating agent. The coating is applied to the surface before contamination. After the surface becomes contaminated, the coating produces a decontaminating agent, which moves toward the surface of the coating and contacts and destroys or neutralizes contaminants that have been deposited on the surface. The present coatings are durable, non-water soluble and non-leaching and can be designed to provide different types of decontaminating agents.

In a particularly useful embodiment of the present coating, the production or the release of the decontaminating agent is triggered by a signal. This is commonly the application of an electrical potential to the coating. This feature provides the advantage that the coating can be applied to a susceptible surface well in advance of a contaminating event and then activated only when needed—usually after a contaminating event has occurred. In a novel embodiment of this system, the coating can be designed to produce the decontaminating agent ultimately from air and water. Thus, after the coating has been activated and after reserves of water and oxygen in the coating have been depleted, those reserves can be restored simply by exposure of the coating to air and/or water. Therefore, the coating can be repeatedly activated, restored by exposure to air and/or water, and activated again and again. Such a feature is very advantageous when the coating is used in areas where it is difficult or dangerous to renew a surface treatment between contaminating events.

Furthermore, the present coating and method does not suffer from deactivation by sunlight, or the effects of heat, which limit the use of many iodine-based decontamination systems. This is because iodine and iodide are photochemically reactive and iodine is volatile, so it tends to diffuse away from the surface being treated into the air when heated.

The present coatings can be adapted to be used on the surfaces of almost any type of substrate. Examples of substrates on which the present coatings can be applied include metal, plastic, wood, fabric, glass, ceramic, or a mixture of any of these. The present coatings and present methods are particularly useful when applied to the surfaces of flexible substrates, such as fabrics and films. In these applications, the present protective coating can be applied to clothing, tents, protective shelters, and the like.

Although almost any substrate is suitable for use with the present coatings and methods, it is preferred that the substrate is one that has a surface that is subject to contamination, such as, for example, a surface that is exposed to the environment. The substrate can be hard, soft, or of almost any texture, and can be composed of almost any material, including, without limitation, metal, plastic, wood, fabric, clay, paper, or the like. Substrates on which the present coatings and methods are commonly useful include tents, protective coverings and shelters, outer surfaces of vehicles and equipment that may be exposed to harmful agents, such as nerve gases, toxins, and biological warfare agents, surfaces for which cleanliness and sterility are important, such as on food preparation and food service equipment and hospital and health service equipment. Furthermore, the coatings and methods of the present invention can be applied over almost any pre-coat that has been applied to a substrate surface, such as, for example, a painted surface.

When the term "surface", or "surfaces", is used herein in relation to a substrate—a material or article on which the subject coating is placed—it means any surface of the material or article that is subject to contamination and for which a decontamination ability is desired. These surfaces are commonly outer surfaces, that is, surfaces of the material or article that are exposed to the surrounding environment. When the term "surface" is used herein in relation to the present coating, it refers to the outer surface of the coating, rather than to the surface of the coating that contacts the substrate or is nearest the substrate.

The present invention includes a coating for a surface, wherein the coating comprises a peroxide source and a peroxide activating catalyst in a durable matrix.

The present invention also includes an electroactivated decontaminating coating comprising a coating which produces a decontaminating agent for a contaminant that is in contact with the coating, where the decontaminating agent is produced when an electrical potential is applied to the coating.

As used herein, the terms "electroactivated decontaminating coating" mean a coating on a surface of a substrate that displays decontaminating properties when an electrical potential is applied to the coating. The application of an electrical potential to the coating in order to generate a decontaminating agent is referred to herein as "electroactivation". Preferably, the coating displays the decontaminating properties to a greater degree during electroactivation than before electroactivation. In one embodiment, the electroactivated coating produces a decontaminating agent, such as an oxidizing agent, when an electrical potential is applied to the coating.

In a preferred embodiment, a component of the present coating is a durable matrix. This can be one or more layers of polymers, gels, resins, or any other structural material that forms a solid, rigid, or gel matrix that is capable of ionic conductance and/or electrical conductance, is not water soluble after curing, and is durable, as discussed below. When it is said that the present coating is capable of ionic conductance, it is meant that electrical charges are able to move through the coating as ionic species. When it is said that the present coating is capable of electrical conductance, it is meant that electrons or holes are able to move through the coating without the movement of ion cores.

It is preferred that the present coating is adherent to the substrate surface and is durable, at least to the extent that the coating, once applied and cured, if curing is required, is resistant to removal due to normal use of the article that has been coated. Furthermore, it is preferred that the coating is not water soluble. As those terms are used herein, a coating is not water soluble if not over 2% by weight of the cured coating dissolves upon submersion in water at 25° C. for 24 hours. It is preferred that not over 1% of the coating dissolves, and more preferred that not over 0.5% by weight of the coating dissolves under those conditions. In a preferred embodiment, the present coating is distinguished from a temporary coating that can be formed on a surface by the application of a foam, a liquid formulation, or the like to the surface. However, in other embodiments of the present invention, the use of foams, liquids, and other such forms may be desirable.

When the present coating is an electroactivated coating that produces hydrogen peroxide as the decontaminating agent, it is preferred that the coating is permeable to water vapor and oxygen. Furthermore, it is preferred that the coating is sufficiently permeable to activated hydrogen peroxide to permit the migration of activated hydrogen peroxide toward the surface of the coating so that the activated hydrogen can contact a contaminant that is present on the surface.

Figure 6:
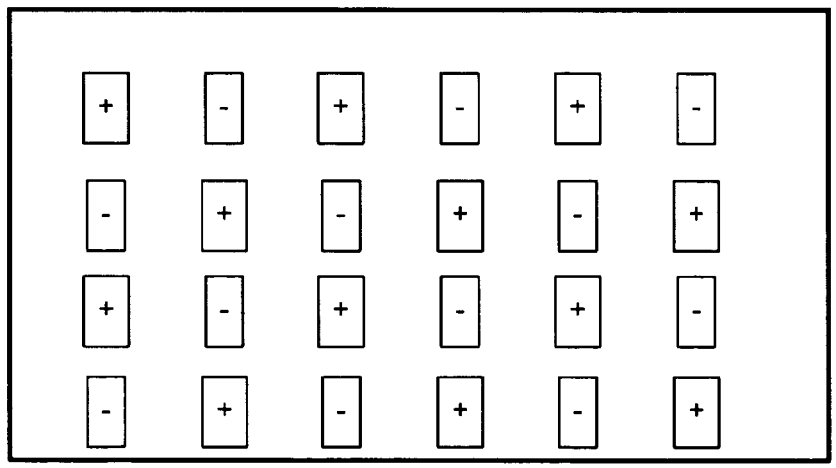
FIG. 6 illustrates the electrode placement for an embodiment of the present coating.

When the present coating is an electroactivated coating, the production of the decontaminating agent can be activated by applying an electrical potential to the coating. In order to supply an electrical potential to the present coating, the coating is preferably placed in contact with a positive electrode and a negative electrode and an electrical potential is established between the electrodes. One or more of each type of electrode can be used, and, in fact, as illustrated in FIG. 6, many electrodes of each type can be provided to be in contact with the coating. Typically, the electrodes are connected via electrode leads to a source of an electrical potential. The electrodes can be constructed integrally with the coating, or the coating can be applied over preexisting electrodes.

The present electroactivated coating is preferably connected through the electrodes to a source of an electrical potential. This can be any source of electrical potential, such as, for example, a battery, line voltage, solar panel, electrical generator, or any other source of electrical potential. However, the use of a battery or any other source of DC current is preferred. It is preferred that direct current be applied to the coating at a low voltage. It is preferable that the voltage is between about −10 volts and +50 volts versus a Ag/AgCl reference electrode, more preferred that it is between about −5 volts and about +25 volts vs Ag/AgCl, even more preferred that it is between about −2 volts and about +5 volts vs. Ag/AgCl, and yet more preferred that it is between about −1 volts and about +2 volts vs. Ag/AgCl.

As used herein, the term "contaminant" means any chemical or biological compound, constituent, species, or agent that through its chemical or biological action on life processes can, if left untreated, cause death, temporary incapacitation, or permanent harm to humans or animals. This includes all such chemicals or biological agents, regardless of their origin or of their method of production. The present method and coating is useful for the decontamination of surfaces that are contaminated with chemical and/or biological warfare agents, as well as with common bacteria, viruses, fungi, or other undesirable chemicals, toxins, or living organisms. Biological warfare agents that can be destroyed by the present invention include, without limitation, bacteria, viruses and fungi, including vegetative and spore forms. These include organisms that produce, or are the causative organisms for, anthrax, smallpox, plague, botulinum toxin, and other diseases. Also included are the chemical toxins that are produced by the organisms.

Chemical warfare agents that can be destroyed by the present invention include, types of nerve gas G, such as the o-alkyl phosphonofluoridates, sarin (GB) and soman (GD), and o-alkyl phophoramidocyanidates, such as tabun (GA); types of nerve gas V, such as o-alkyl, s-2-dialkyl aminoethyl alkylphosphonothiolates and corresponding alkylated or protonated salts, such as VX; vesicants, such as the mustard compounds, including 2-chloroethylchloromethylsulfide, bis (2-chloroethyl)sulfide, bis(2-chloroethylthio)methane, 1,2-bis(2-chloroethylthio)ethane, 1,3-bis(2-chloroethylthio)-n-propane, 1,4-bis(2-chloroethylthio)-n-butane, 1,5-bis(2-chloroethylthio)-n-pentane, bis(2-chloroethylthiomethyl) ether, and bis(2-chloroethylthioethyl)ether; Lewisites, including 2-chlorovinyldichloroarsine, bis(2-chlorovinyl) chloroarsine, tris(2-chlorovinyl)arsine, bis(2-chloroethyl) ethylamine, and bis(2-chloroethyl)methylamine; saxitoxin, ricin, alkyl phosphonyidifluoride, alkyl phosphonites, chlorosarin, chlorosoman, amiton, 1,1,3,3,3,-pentafluoro-2-(trifluoromethyl)-1-propene, 3-quinuclidinyl benzilate, methylphosphonyl dichloride, dimethyl methylphosphonate, dialkyl phosphoramidic dihalides, dialkyl phosphoramidates, arsenic trichloride, diphenyl hydroxyacetic acid, quinuclidin-3-ol, dialkyl aminoethyl-2-chlorides, dialkyl aminoethan-2-ols, dialkyl aminoethane-2-thiols, thiodiglycols, pinacolyl alcohols, phosgene, cyanogen chloride, hydrogen cyanide, chloropicrin, phosphorous oxychloride, phosphorous trichloride, phosphorus pentachloride, alkyl phosphites, sulfur monochloride, sulfur dichloride, and thionyl chloride.

The decontaminating agent of one embodiment of the present invention is preferably a molecule or compound that is produced within the coating when an electrical potential is applied to the coating, is mobile within the coating to the extent required for the agent to come in operable contact with a contaminant that contacts the outer surface of the coating, and acts upon the contaminant to destroy or neutralize the contaminant.

Examples of useful decontaminating agents include reactive oxygen species, such as hypochlorites, including sodium hypochlorite, chlorine, potassium peroxymonosulfate, ammonium persulfate, ammonium peroxymonosulfate, peroxydisulfate, permanganates, including potassium permanaganate, peroxides, such as hydrogen peroxide, and nucleophilic active agents, such as hydroxide, and the mono- and di-anions of hydrogen peroxide. The nucleophiles may be bound to a catalyst such as a metal complex.

In a preferred embodiment, the decontaminating agent is hydrogen peroxide and one or both of its deprotonated forms, and activated hydrogen peroxide is particularly preferred. Activated hydrogen peroxide is typically hydrogen peroxide or one of its anionic forms bound to a metal catalyst. It is believed that the resulting complex of the peroxide with the metal catalyst is better able to destroy contaminants through one or more of the following reactions: peroxidation, oxidation, perhydrolysis, and hydrolysis.

In order to obtain activated peroxide, it is preferable to include a peroxide activating catalyst in the coating. Examples of useful peroxide activating catalysts include complexes of ethylenediaminetetraacetic acid with metals such as iron (EDTA/Fe complexes), tetraamidomacrocyclic ligand (TAML®) complexes with metals such as iron (TAML®/metal complexes are exemplified by the compounds described in U.S. Pat. Nos. 5,847,120, 6,051,704, 6,011,152, 6,100,394 and 6,054,580), manganese gluconate, sodium hypochlorite, N-[4-(triethylammoniomethyl)benzoyl]-caprolactam chloride, nonanoyloxybenzene sulfonate, porphyrins, phthalocyanines, ruthenium oxide, indium oxide, quinones, and the like. Examples of porphyrins and phthalocyanines that are useful as the peroxide activating catalyst in the present method include those shown in FIG. 1. Peroxide activating catalysts of the present invention include TAML®/metal complexes, and TAML®/Fe complexes. The peroxide activating catalyst can be located anywhere in the present coating. For example, it could be distributed throughout the matrix layer, or contained in a surface layer that was formed over the top of the matrix layer. Alternatively, it can be linked to, adsorbed onto, or otherwise affixed to the substrate over which the coating is applied. In one embodiment, the peroxide activating catalyst is chemically linked to the gel or to the polymer layer, whereas in other embodiments, the peroxide activating catalyst is blended with the gel and/or with the outer polymer layer. It should be recognized that the gel of the present invention can be a polymer. The "polymer layer", as those terms are used herein, refers to a layer that is different from the gel.

The peroxide activating catalyst can be linked to the gel and/or the polymer layer by a chemical linkage, or by electrostatic force, or by adsorption into pores. A chemical linkage between the peroxide activating catalyst and the gel and/or the polymer layer can be formed by any of several chemical linkage methods known in the art. An important feature of such a linkage is the stability or inertness of the linkage, and the conjugates forming the linkage, to oxidation by hydrogen peroxide under the conditions found in the activated coating. Stability is provided by alkane- or amide-based linkers that join the catalyst to the gel or the polymer layer, and amine and carboxylic acid groups form the basis of many suitable catalyst/gel or catalyst/polymer conjugates, as will alkanes derived from intermediates that comprise substituted olefins.

Examples of methods that are useful for chemically linking the catalyst to the gel or the polymer layer include: (a) reaction of a benzylchloride (on the gel or the polymer layer) with a primary amine (pendant from ligand or complex of the catalyst) to give a secondary amine, which may be further reacted to give a hindered tertiary amine or quaternary amine for enhance stability or inertness; (b) reaction of a benzoic acid moiety (in a gel or a polymer layer) with a carboxylic acid or a nitrile pendent from the catalyst or a ligand attached to the catalyst. Other such linking methods are well known in the art.

In an alternative approach, the peroxide activating catalyst can be immobilized in a stable cation- or anion-exchange membrane. By way of example, the placement of a quaternary amine functional group on the catalyst to give a net positive charge could be followed by introducing the charged catalyst into an oxidatively stable ion exchange polymer membrane such as Nafion®. In a like manner, a negatively charged catalyst could be obtained by addition of sulfonate, carboxylate, phenolate or amine diacetate groups to the catalyst structure, and the negatively charged catalyst could be introduced into an anion exchange membrane containing tertiary or quaternary ammonium groups. Either of the catalyst/ionomer films described above could be laminated onto the surface of the peroxide generating electrodes or coated onto the electrodes from a polymer solution followed by drying and/or annealing.

Figure 2:
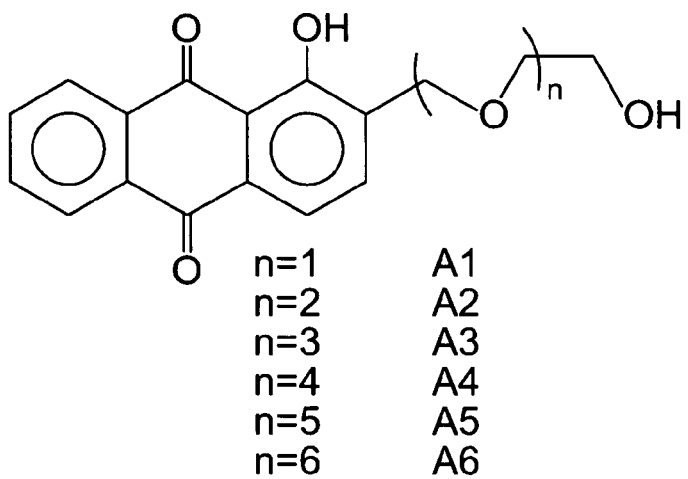
FIG. 2 shows examples of substituted anthraquinones that are useful as the mediator in an embodiment of the present method.

In embodiments of the present coating where activated hydrogen peroxide is the decontaminating agent, it is preferred that one or more mediators are included. As used herein, a mediator is to be understood to be a compound or molecule which is involved in the transfer of electrons and hydrogen ions to oxygen in the formation of hydrogen peroxide. Preferably, the mediator is a compound that can be reversibly oxidized and reduced and can transfer hydrogen ions and electrons in a chemical reaction. Examples of useful mediators for the present coating and method include quinones, naphthaquinones, and anthraquinones. The quinones and anthraquinones can be substituted or unsubstituted. Examples of useful mediators include quinones, naphthoquinones, anthraquinones, and their derivatives. Mixtures of any of these can also be used. An example of a substituted anthraquinone that can be used as a mediator in the present method has a structure as shown in FIG. 2.

Figure 3:
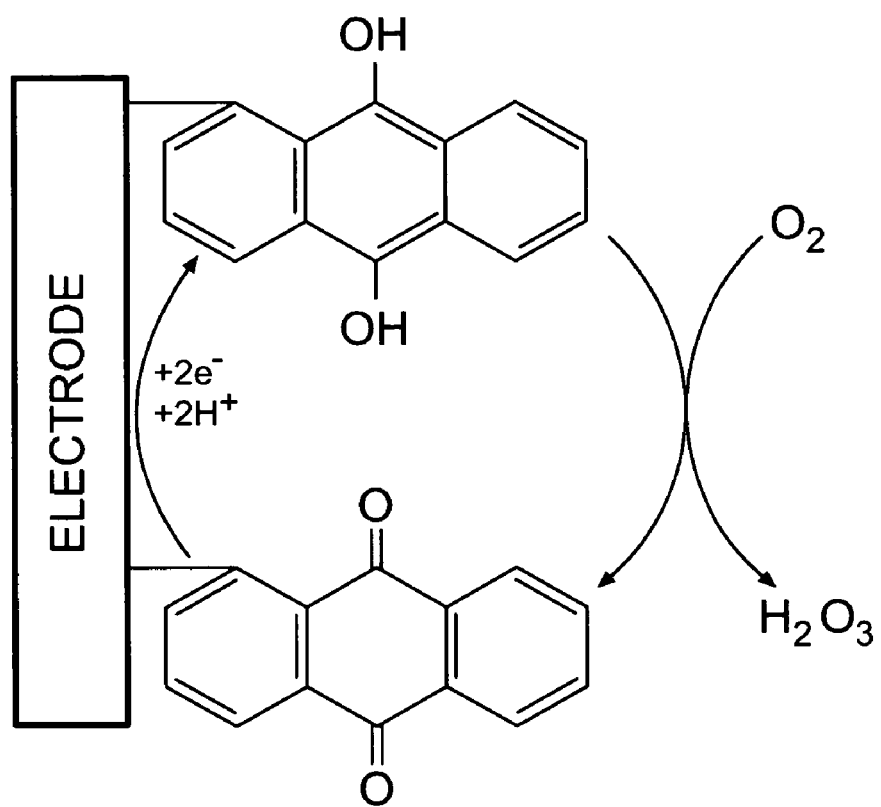
FIG. 3 illustrates the attachment of anthraquinone to an electrode and, shows its action in transferring hydrogen ions and electrons in the reaction to produce hydrogen peroxide with the reduction of oxygen in an embodiment of the present method.

The mediator can be attached to an electrode and/or it can be distributed throughout the matrix of the coating. FIG. 3 illustrates the attachment of anthraquinone to a cathode, which can be a carbon electrode, and the function of the anthraquinone in transferring hydrogen ions and electrons from the cathode to oxygen for the production of hydrogen peroxide. In one embodiment, the electrode with bound anthraquinone could be attached to the substrate and covered with the matrix layer. Imposition of an electrical potential at the electrode would cause the reduction of anthraquinone to 4,9-dihydroxyanthracene. Oxygen diffusing through the matrix layer would then be reduced by the 4,9-dihydroxyanthracene to hydrogen peroxide and would oxidize the 4,9-dihydroxyanthracene back to anthraquinone. The cycle could then be repeated for as long as the electrical potential remained imposed on the coating and oxygen was available at the electrode.

Figure 4A:
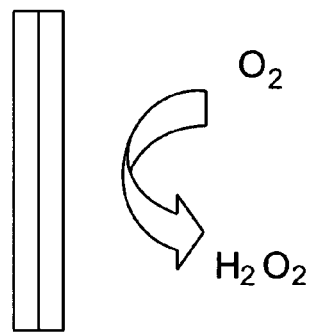
FIG. 4 is an illustration of the generation of hydrogen peroxide at electrodes having no mediator (A) and having an attached mediator (B)
Figure 4B:
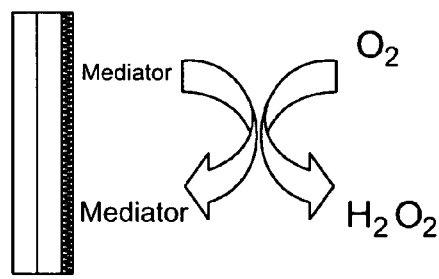

FIG. 4 is an illustration of the electroactivated production of peroxide and in FIG. 4(A) shows that the reaction can take place at the electrode in the absence of a mediator. FIG. 4(B) shows the same reaction, but as catalyzed by the presence of a mediator.

As used herein, the term "decontaminate" means to change a contaminant from a form or an amount that is harmful to a human or an animal to a form or an amount that is less harmful to the human or animal by any degree. Preferably, when a contaminant is decontaminated, it is rendered substantially harmless to humans or animals that come into contact with it after decontamination is completed. When used herein in the context of decontamination of a contaminant, the term "destroy" means the modification of the chemical structure of the contaminant to a chemical form that is less harmful to humans or animals than the original structure, and the term "neutralize" means the combination of the contaminant with another compound or material that binds or dilutes the contaminant, or activating catalyst that activates the peroxide. The activated peroxide can then migrate to the surface of the coating and contact and oxidize any contaminant (shown here as a chemical/biological warfare agent, "CBWA") present on the surface to decontaminate the surface.

The switch that is used to control the activation of the present coating can be manually activated, or it can be activated by a signal from a sensor. When the present coating is combined with a switch that is activated by a sensor, a sensor-activated decontaminating coating system is formed. Such systems are within the scope of the present invention.

Sensor-activated decontaminating coating systems of the present invention can include an electroactivated decontaminating coating according to any one of the electroactivated coatings that are described herein, a source of an electrical potential, electrode leads interconnecting the source of an electrical potential and the electrodes of the coating, a switch that is located in an electrical lead and which controls the application of an electrical potential to the coating, and a sensor that controls the operation of the switch. The sensor can be one that senses the presence of a contaminant, and in a preferred embodiment, the sensor senses the presence of a chemical warfare agent and/or a biological warfare agent. In a preferred embodiment, the sensor closes the switch to activate the subject coating when it senses the presence of a contaminant. The sensor optionally opens the switch after a predetermined amount of time has elapsed, or in response to some other indication. When the switch is opened, the activation of the coating ceases.

The electrodes that are used in the present invention can be formed from any electrically conductive material. Examples of suitable electrode materials include metals, such as platinum (in any form, but including without limitation, plate form, in ring-disk configuration, as a foil, and as nanoparticles), gold (with or without surface modification), metal oxides, such as indium tin oxide, conductive metal salts, carbon, carbon/metal composites, intrinsically conductive polymers, materials that include carbon nanotubes, and mixtures of any of these materials. In preferred embodiments, the electrodes can be formed from carbon/metal composites, such as carbon/platinum, intrinsically conductive polymers, or materials that include carbon nanotubes.

One or both of the electrodes is optionally coated with a polymer, such as a fluorinated sulfonic acid copolymer, an example of which is Nafion®, in order to reduce or prevent the decomposition of hydrogen peroxide. Preferably, the anode is optionally coated with a fluorinated sulfonic acid copolymer, such as Nafion®.

The electrode leads of the present invention can be of any material that is commonly used for electrode leads in the art. For example, the electrode leads can be formed from a metal, such as silver or copper, or from an electrically conductive metal compound, or from carbon, or from an intrinsically conductive polymer, or the like.

An example of a coating of the present invention includes a positive electrode and a negative electrode; which are interconnected by a water insoluble matrix which is electrically conductive or ionically conductive. The coating also includes a mediator that is selected from a substituted or unsubstituted quinone or anthraquinone and which is present in the matrix or bound to an electrode, and a peroxide activating catalyst that is selected from EDTA/Fe complex or TAML®/metal complex or other metal complexes known to activate peroxide in a catalytic manner. The coating also includes electrode leads for interconnecting the positive electrode and the negative electrode with a source of electrical potential.

The present coatings can be produced by any technique that is suitable for the formation of the structures that are described herein. In one embodiment, an electroactivated decontaminating coating is produced by applying at least one positive electrode and at least one negative electrode to a surface of a substrate. The electrodes can be of the same or different materials of construction and can be produced from any of the electrode materials described above. Preferably, the electrodes are carbon/Pt composites, or intrinsically conductive polymers, or materials otherwise renders it less available to harmful interaction with the biological system of a human or animal with which it comes in contact.

In a preferred embodiment of the present invention, the decontaminating agent is a peroxide. It is preferred that the present coating provides a peroxide source. The peroxide source optionally comprises a reservoir of a peroxide, or a signal activated peroxide producing system.

As used herein, a "signal activated" peroxide producing system is a system that produces a peroxide in response to a signal. A preferred signal for activating the present coating is the application of an electrical potential to some portion or all of the coating. In a signal activated system, the decontaminating agent is produced when the electrical potential is applied to the coating. The agent can be produced by being freed from a reservoir, or it may be synthesized by chemical reactions within the coating. When the agent is the product of an electrical potential, the signal activated peroxide producing system includes a positive electrode and a negative electrode, which are interconnected by an electrically or ionically conductive matrix that contains water and/or oxygen.

Figure 5:
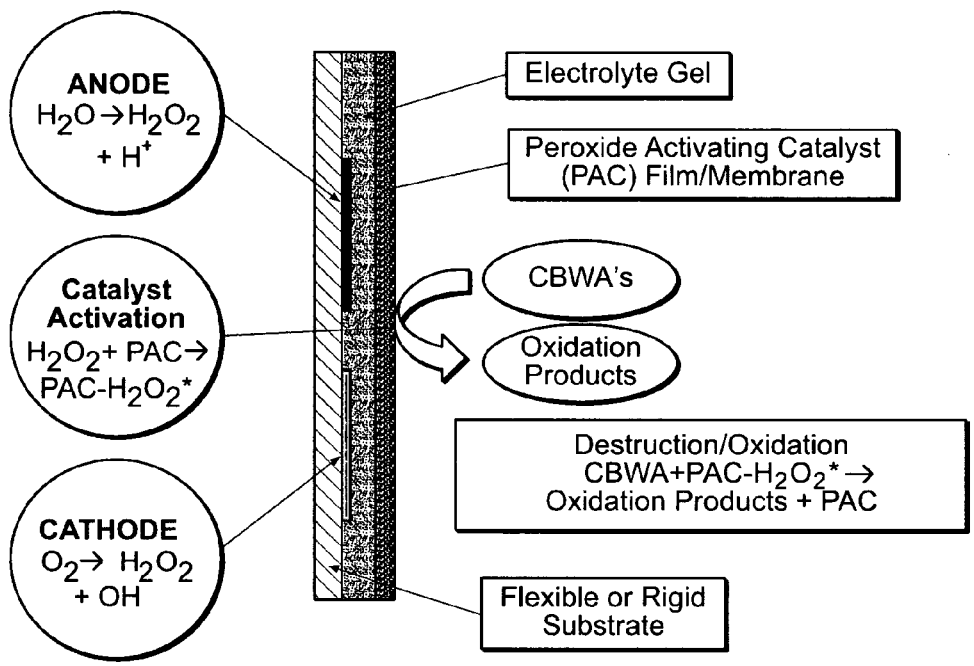
FIG. 5 is an illustration of the structure and action of an embodiment of the present coating in which electrodes are applied to a substrate and covered with a matrix, shown here as an electrolyte gel, which includes a peroxide activating catalyst that produces activated hydrogen peroxide that migrates toward the surface of the coating and destroys contaminants that are in contact with the surface of the coating.

An embodiment of an electroactivated decontaminating coating of the present invention is illustrated in FIG. 5. In this embodiment of the present coating, hydrogen peroxide is produced at both anode and cathode in response to an electrical potential. At the anode, hydrogen peroxide is produce by the oxidation of water. At the cathode, it is produced by the reduction of oxygen. Although not shown, the system can further comprise electrode leads that interconnect the electrodes with appropriate poles of a source of an electrical potential. This system can optionally include a switch that can be located in the positive electrode lead or the negative electrode lead, or anywhere else in the electrical system so that the switch can control whether or not an electrical potential is applied to the electrodes. As illustrated in FIG. 5, hydrogen peroxide is produced at the electrodes. The peroxide then diffuses into the matrix, referred to in FIG. 5 as "electrolyte gel", where it encounters peroxide that comprise carbon nanotubes. The electrodes can be applied by any method that is known in the art.

When carbon nanotubes are used in an electrode, the electrodes may be fabricated by spin coating carbon nanotubes on the surface of the substrate. They may be applied directly onto previously applied carbon electrode surfaces, and they may be applied as a mixture in solution with, for example, nafion and/or teflon, or in solution with polyethylene. As an alternative, carbon nanotubes can be intermixed into an ink normally used for screen printing and the electrode can be applied by screen printing with the ink containing the carbon nanotubes. As another alternative, the electrodes may be formed by electro-polymerization of polypyrrole with carbon nanotubes, or by combining carbon nanotubes with sol-gel techniques to generate porous electrode materials. It is preferred, however, that the electrodes are applied by screen printing.

The second step of the method is applying a layer comprising a matrix that is electrically conductive or ionically conductive over the positive electrode and the negative electrode, wherein the matrix contains a peroxide activating catalyst and is permeable to oxygen, water vapor, and hydrogen peroxide. The matrix is then cured, if curing is required. The matrix can be applied by any method that is known in the art, but it is preferred that the matrix is applied by screen printing.

In either of the steps discussed above, the application of the coating can involve the application of one or more layers to the surface in one or a series of steps.

After application of the electrodes and the matrix, the matrix is permitted to accumulate oxygen and water, and electrode leads are connected between the electrodes and appropriate terminals of a source of an electrical potential, such as a battery. When a sufficient amount of oxygen and water have accumulated in the coating, it is ready for activation.

In those embodiments where it is desirable to use a peroxide activating mediator, the mediator can be optionally applied to one or more of the electrodes, or it can be distributed throughout the matrix. Alternatively, the mediator can be provided both bound to an electrode and distributed throughout the matrix, or bound to or integral to the outer surface of the coating.

The present invention also includes a method of producing activated peroxides in a coating. The novel method comprises providing a coating comprising a peroxide source and a peroxide activating catalyst; causing the peroxide source to produce a peroxide; and contacting the peroxide with the catalyst to produce activated peroxide.

The peroxide source optionally comprises a reservoir of a peroxide, or a signal activated peroxide producing system. As discussed above, in a preferred embodiment, the peroxide is hydrogen peroxide and the peroxide source is a signal activated peroxide producing system, which includes a positive electrode and a negative electrode, which are interconnected by an electrically or ionically conductive medium that comprises water and/or oxygen.

The step of causing the peroxide source to produce the hydrogen peroxide can be carried out by providing a signal to activate the production of hydrogen peroxide. Preferably, the signal is the imposition of an electrical potential across the positive and the negative electrode, thereby causing the reduction of oxygen and the production of hydrogen peroxide.

In order to facilitate the formation of hydrogen peroxide at an electrode, it is preferred that the peroxide source further includes a mediator which is involved in the transfer of electrons and hydrogen ions to oxygen in the formation of hydrogen peroxide. Examples of preferred mediators include quinone and anthraquinone.

Figure 7:
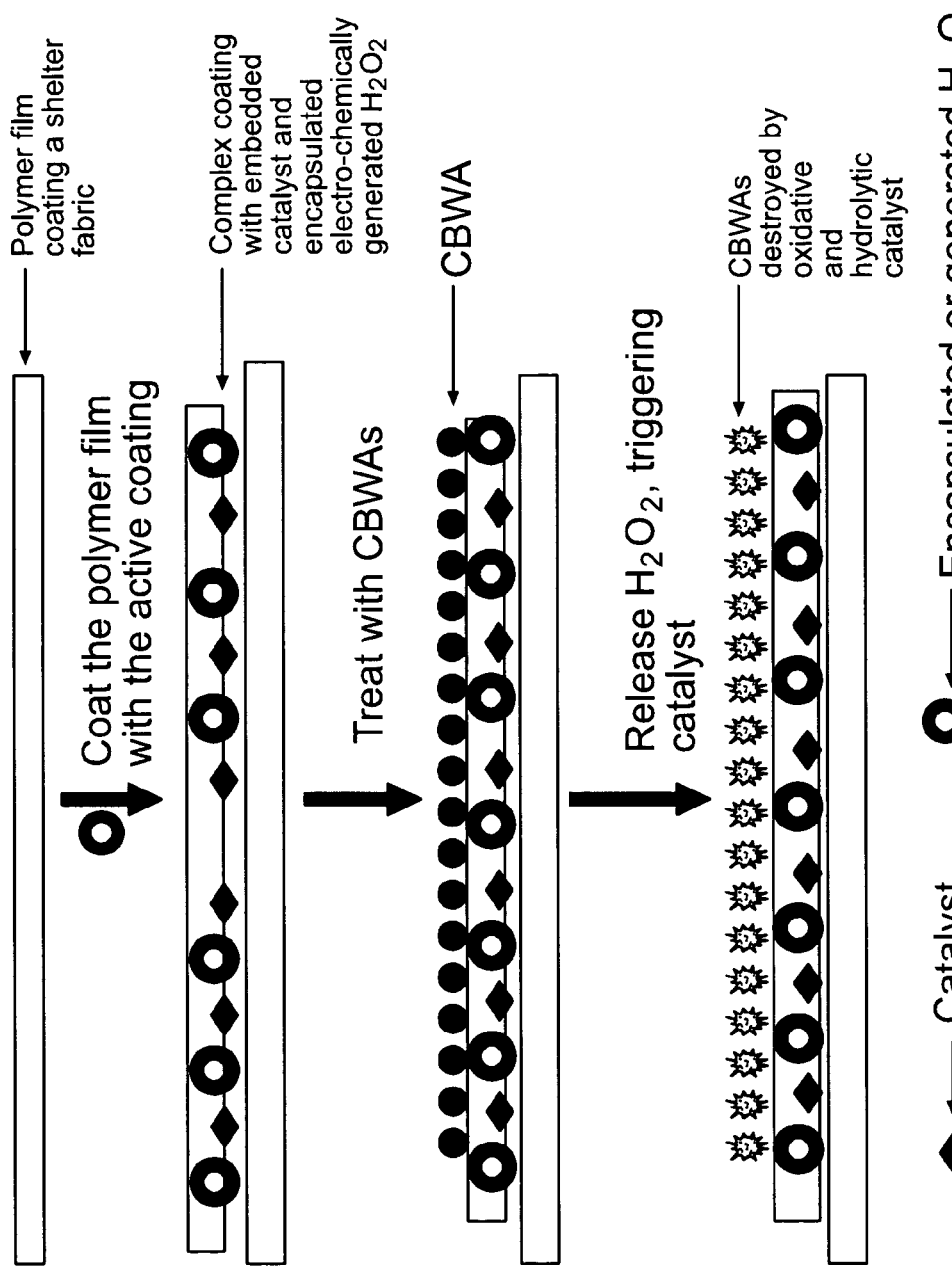
FIG. 7 and FIG. 8 are illustrations of the overall concept of alternative embodiments of the present invention.
Figure 8:
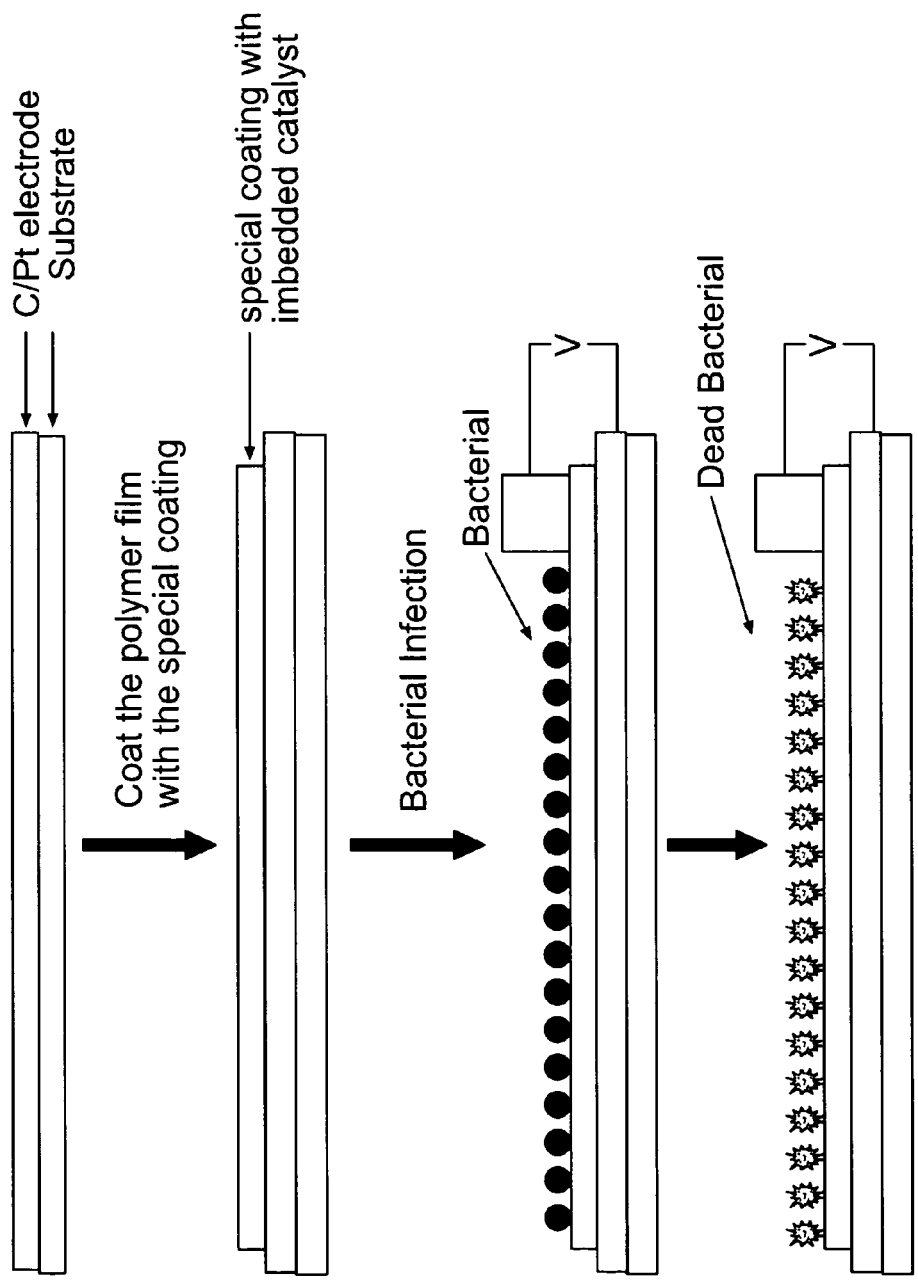

The present invention also includes a method of decontaminating a surface of a substrate that is susceptible to contamination with a contaminant. The method involves applying to the surface a coating which produces a decontaminating agent for the contaminant when an electrical potential is applied to the coating, connecting the electroactive coating to a source of an electrical potential; and when the surface is contaminated, applying an electrical potential to the electroactive coating, thereby producing the decontaminating agent and destroying the contaminant. An illustration of an embodiment of the method of the invention is shown in FIG. 7, where a coating of the present invention is applied to a polymer film covering a shelter fabric. The novel coating is illustrated to contain a peroxide activating catalyst and either microencapsulated or electrochemically generated hydrogen peroxide. Contaminants, illustrated in FIG. 7 as CBWA's, on the surface of the coating are then destroyed by action of the activated hydrogen peroxide. A similar concept is illustrated in FIG. 8, in which a source of electrical potential (V) is shown to be connected to the novel coating.

As discussed above, the contaminant can include a chemical warfare agent, a biological warfare agent, a bacterial toxin, a disease causing microorganism, or a mixture of any of these.

The present method can further include the step of ceasing the application of an electrical potential to the electroactive coating, thereby ceasing the production of the decontaminating agent. After the electrical potential is removed, the coating can be exposed to air and oxygen is permitted to enter the coating from the air. Also, water vapor can be permitted to enter the coating. After oxygen and water are restored to the coating the step of applying an electrical potential to the electroactive coating, thereby producing the decontaminating agent and destroying the contaminant can be repeated.

Articles that have been coated with a coating of the present invention are also included within the scope of the invention.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

EXAMPLE 1

This example illustrates the electrically activated generation of hydrogen peroxide in a water solution and subsequent activation of the peroxide by a peroxide activation catalyst.

In this example, hydrogen peroxide was generated at electrode surfaces and quinone was included as a mediator. The generation of hydrogen peroxide was shown by the oxidation of iodide ions to iodine and the subsequent reaction of iodine with starch to form a blue color complex.

In a detailed procedure, hydrogen peroxide ($H_2O_2$) was generated electrochemically in an acidic aqueous solution (0.5M $Na_2SO_4$ with the pH value adjusted to about 1.8 with 0.1 M $H_2SO_4$). Pt foil (1 $cm^2$) was used as the working electrode and the counter electrode, and −0.6 V via SCE was applied during the reaction. Air as the source of oxygen was bubbled through the solution during the reaction. In the absence of hydroquinone (HQ), $H_2O_2$ was generated slowly and only a small amount of $H_2O_2$ was generated after 3 hours. However $H_2O_2$ was generated in 10 seconds when 0.001 M HQ was added. The combination of potassium iodide and starch was used to detect the formation of $H_2O_2$. When $H_2O_2$ is generated, iodide was oxidized to iodine which then reacted with starch to form a blue complex. The appearance of blue color in the in the solution demonstrated the formation of $H_2O_2$.

EXAMPLE 2

This example illustrates the fabrication of several embodiments of the coating of the present method and demonstrates the feasibility of generating hydrogen peroxide in an aqueous solution and in a coating.

Materials and Instrumentation:

A carbon paste that contained platinum was coated onto a plastic sheet by screen printing. Indium tin oxide was coated onto PET sheet that was obtained from Delta Technologies. Platinum and gold foils from Aldrich were used as received. Nitrogen and oxygen used were of high purity. Hydrogen peroxide (30%), potassium iodide, calcium chloride, starch, sodium sulfate, hydroquinone, sodium hydroxide, sulfuric acid, alginate acid sodium salt, poly(diallydimethylammonium chloride) (PDDA), Nafion, and poly(sodium 4-styrenesulfonate) (PSSNa) were used as received from Aldrich. Pyrrole received from Aldrich was distilled before used.

A biopotentiostat (PCI4 Potentiostat/Galvanostat/ZRA, available from Gamry Instrument) was used in all the electrochemical experiments along with a three electrode system that included a SCE reference electrode, a counter electrode, and a working electrode. For the working electrode, both platinum foil and carbon with platinum on a plastic sheet with a size of 1 cm×1 cm were used. For the carbon electrode, a screen printed electrode was used. Sodium sulfate aqueous solution (0.5 M) with pH of 2 was used in all of the experiments. For the control experiment, pure nitrogen was bubbled through the solution before and during the experiment whereas oxygen was bubbled through the aqueous solution before and during the experiment for the generation of hydrogen peroxide.

A UV-Vis spectrometer with a dip probe (USB200, available from Ocean Optics) was used to detect the formation of a blue complex from starch and iodine. The formation of the blue complex was the method used to detect the electrochemical generation of hydrogen peroxide. The basis for the test is that hydrogen peroxide oxidizes iodide immediately to produce triiodide, which then reacts with starch to form a visible blue complex. An Olympus 470 digital Camera was used to record the color change when the blue complex was formed.

Fabrication of a Multi-layer Coating on the Surface of the Electrode:

Three approaches were evaluated for the formation of a hydrogel coating on the surface of the electrode.

Approach 1: The electrodes were coated with multilayer of PDDA/PSS. In a typical example, a tin-doped indium tin oxide (ITO) electrode was cleaned by sonicating the electrode sequentially for about 10 min each in methanol, in ethanol containing 5% of sodium hydroxide, and distilled water. The cleaned ITO was then treated with an aqueous solution in a weight ratio of 1:1:5 ($H_2O_2$:$NH_3$:$H_2O$) at 70° C. for 30 minutes. The cleaned ITO electrodes were kept in absolute methanol in plastic containers and were rinsed with water before use. Separate aqueous solutions containing 2.5% by weight of PDDA or PSSA were prepared for forming the multilayer on the surface of the electrode. After the PDDA solution was prepared, the pH of the solution was adjusted to 2.0 by adding a diluted HCl solution. In a complementary manner the pH of the PSSNa solution was adjusted to 9.5 by adding a 5% sodium hydroxide aqueous solution. In the first step of the coating experiment, the ITO electrode was immersed in the PDDA solution for 30 mins, then washed with DI water, immersed in DI water for another 30 mins, and finally dried in air for one hour. In the second step the PDDA coated ITO electrode was immersed in the PSSNa solution for 30 mins, washed with DI water, immersed in DI water for another 30 mins, and dried in air for one hour again. By repeating those two steps, a thin film with a multi-layer of PDDA/PSSNa was prepared on the surface of the ITO electrode. A multi-layer made of either 5 or 15 PDDA/PSSNa layers was prepared with this process.

Approach 2: A multi-layer coating of PDDA/Alginate was formed on the surface of ITO electrode by using a procedure that was similar to Approach 1, as described above, except that the PSSNa aqueous solution was replaced by 0.5% of alginate acid sodium solution.

Approach 3: In the third approach, a PDDA/Alginate multi-layer containing HQ, KI and starch was coated on the surface of the electrode. During the preparation, HQ, KI and starch were added to 0.5% alginate acid sodium solution and the formed solution was used to make the multi-layer coating.

A dye molecule was also incorporated into the multilayer coating by soaking the coated ITO electrode in a dye aqueous solution over night. This method was also used to incorporate hydroquinone into the multi-layer on ITO electrode, replacing the dye solution with hydroquinone aqueous solution.

Applying a Nafion® Layer on the Surface of the Carbon Electrode:

An aqueous solution containing Nafion® (0.05 ml) was spread onto the surface of a Carbon/Pt electrode (1 cm×0.25 cm) and a thin layer of Nafion® formed on the surface of the electrode after it was dried in air for 1 hour. This Nafion® coated carbon/Pt electrode was used as the counter electrode for the experiment to generate the hydrogen peroxide.

Electrochemical Generation of Hydrogen Peroxide from the Electrodes Having Multi-layer Coatings:

The multi-layer coated ITO electrode was used as the working electrode to generate hydrogen peroxide. The experimental procedure was same as the one mentioned above.

Results and Discussion:

Generation of Hydrogen Peroxide in Solution:

In general, the protocol for the generation of hydrogen peroxide was patterned after the methods described in Collins, T. J. et al., The Development of Green Oxidants, Extended Abstract of Plenary Lecture, 1997, Green Chemistry and Engineering Conference, Implementing Vision 2020 for the Environment, National Academy of Sciences, Washington, D.C., Jun. 23-25 (1997), Sljukic, B. et al., *Journal of the Iranian Chemical Society*, (2):1-25 (2005), Banks, C. E. et al., *Journal of the Iranian Chemical Society*, (2): 60-64 (2005), Qiang, Z. et al., *Water Research*, (36):85-94 (2002), Pletcher, D.; *Electrosynthesis*, (1):4 (1999), and DuVall, S. H. and McCreery, R. L., *J. Am. Chem. Soc.*, (122):6759-6764 (2000). The goal was to establish a protocol for generating hydrogen peroxide at the electrode and then detecting the generated hydrogen peroxide with a UV-Vis spectrometer.

Reduction of oxygen is the most common method used to generate hydrogen peroxide electrochemically. In this method, oxygen is reduced on the cathode to form hydrogen peroxide as shown below:

$$O_2+2H_2O+2e^- \text{---} H_2O_2+2OH^- \tag{1}$$

or $$O_2+2H^++2e^- \text{---} H_2O_2 \tag{2}$$

An advantage of this method is that it can be performed at a broad pH range.

The selections of electrode materials and reaction conditions are believed to be important for the generation of hydrogen peroxide, because an important feature for an efficient decontamination device is fast response to a CBWA. This is believed to require a high generation rate of hydrogen peroxide. It was believed that oxygen reduction to form hydrogen peroxide occurs in high yield at cathodes that include mercury, gold and carbon. Thus carbon and carbon containing platinum and ITO were selected as the electrode materials for an initial test.

In initial attempts to generate hydrogen peroxide in a classical liquid electrolyte electrochemical cell with a plate electrode (Scheme 1), it was found that the generation rate of hydrogen peroxide was extremely slow due to the limited solubility of oxygen in the reaction media. To overcome this problem, air was bubbled through the cell before and during the reaction. In the first set of the experiments, the electrodes were immersed in a sodium sulfate aqueous solution (0.5 M) with pH of 2 and –0.6 V was applied to the working electrode during the experiments. Several working electrodes were tested. After a measured time had passed an aliquot of the test solution was added to an aqueous solution of potassium iodide and starch to visually detect the formation of blue color, which indicates the generation of hydrogen peroxide according to the scheme:

$$H_2O_2 + I^- \quad H_2O + I_2 \tag{1}$$

$$I_2 + I^- \quad I_3^- \tag{2}$$

$$I_3^- + \text{starch} \quad \text{Complex with Blue Color} \tag{3}$$

In the present test, no color change was observed after 1 hour for each of the electrodes used in the experiment. This suggested that the generation of hydrogen peroxide was extremely slow.

Detection of Hydrogen Peroxide.

Figure 9:
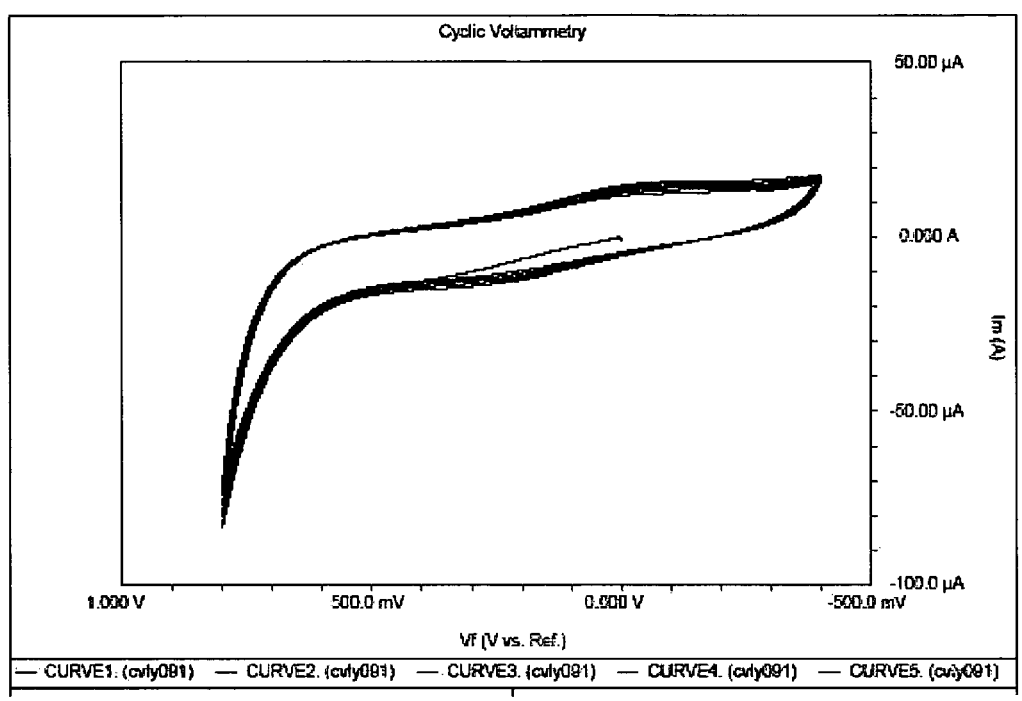
FIG. 9 shows a cyclic voltammogram of 10 mmol/liter hydroquinone at the surface of a platinum electrode, where redox peaks are observed at −0.02V and 0.24V for a three electrode system (SCE reference electrode and platinum counter and working electrodes) in 0.5 M $Na_2SO_4$ at pH=2, adjusted with $H_2SO_4$, and with air as an oxygen source.

Catalysts in solution can accelerate the generation of hydrogen peroxide electrochemically on the surface of the electrode. The most commonly used catalysts for electrochemically generating hydrogen peroxide are hydroquinone, porphyrins and carbon nanotubes. Hydroquinone was selected for testing in this scheme, but other derivatives of hydroquinone such as discussed above for use as mediators may prove useful also. The hydroquinone catalysis mechanism is illustrated in FIG. 3 and cyclic voltammograms of hydroquinone on platinum electrode in sodium sulfate aqueous solution (0.5M) with pH of 2 is shown in FIG. 9. Two redox peaks are observed at −0.02V and 0.24V, respectively.

Figure 10:
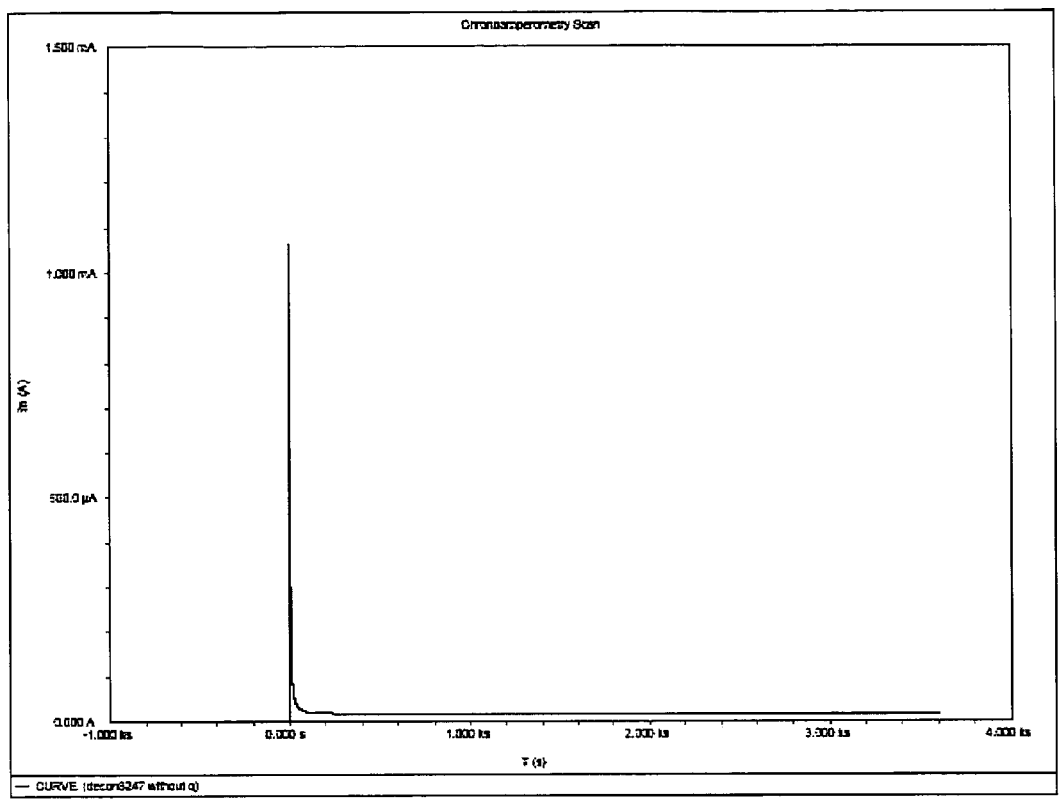
FIG. 10 is a graph showing current vs. time response for electrochemical synthesis of hydrogen peroxide at the surface of a platinum electrode under conditions of 0.5 M $Na_2SO_4$ as the electrolyte; pH=2, adjusted with $H_2SO_4$, and using a three electrode system (SCE reference electrode and platinum counter and working electrodes), with air as the oxygen source and at a voltage of −0.6V.
Figure 11:
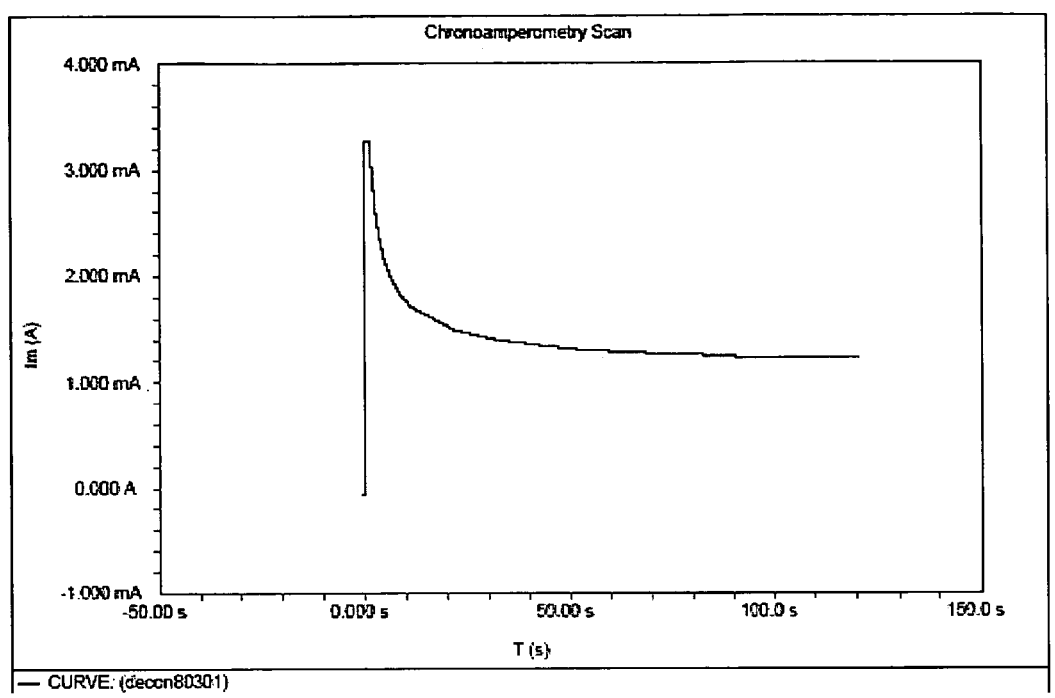
FIG. 11 is a graph showing current vs. time response for electrochemical synthesis of hydrogen peroxide at the surface of a platinum electrode under the same conditions as described for FIG. 10, except that 10 mmol/liter hydroquinone was present.

Table 1 shows the generation of hydrogen peroxide in the solution that was observed for different electrodes after 1 hour. With a C/Pt electrode, the color change was apparent after only 15 minutes. As shown in FIGS. 10 and 11, the reduction current at the Pt electrode dramatically increased when hydroquinone was added to the reaction media. Although electrochemical generation of hydrogen peroxide in the solution was observed, the generation rate was slow.

TABLE 1

Summary of the generation of $H_2O_2$ at different electrodes.

| No | Electrode | Size | Time for Color Change* |
|---|---|---|---|
| 1 | Carbon | 0.9 cm (diameter) | 1 hr |
| 2 | Carbon/Pt | 0.5 mm × 0.5 mm | 15 min |
| 3 | Pt Foil | 0.5 mm × 0.5 mm | 1 hr |
| 4 | ITO on Plastic | 0.5 mm × 0.5 mm | 1 hr |

*Color change observed after addition of aliquot from electrochemical cell added to starch indicator solution.

The generation of hydrogen peroxide could be related to the oxidation of peroxide at the anode. To better visualize the electrochemical formation of hydrogen peroxide, a Pt foil was used as the working electrode and an aqueous solution of KI and starch was added to the solution. The characteristic blue color was observed one minute after −0.6V was applied to the working electrode. To rule out the electrochemical oxidation of iodide to iodine, the same experimental conditions were used, except that air was not bubbled through the solution. In that situation, no blue color was observed.

Coating Nafion® on the Surface of the Anode to Prevent Hydrogen Peroxide Decomposition:

Nafion® is one of a series of fluorinated sulfonic acid copolymers (Nafion® is a registered trademark of the DuPont company), and also the first synthetic ionic polymer. Nafion® is both chemically inert and permselective to cations, preventing the transport of anions across films cast from it. It is widely used as the membrane in electrochemical systems. Traditional electrochemical generation systems use ion-selective membranes to separate the anode and cathode. The reaction solutions in the anode side and cathode side can be separated by an anion selective membrane and this membrane can prevent the diffusion of hydrogen peroxide through the cathode side to the anode side, and no decomposition of hydrogen peroxide should occur.

Because the rate of the overall generation of hydrogen peroxide may be affected by oxidation of peroxide species at the anode, the anode surface was coated with a layer of Nafion® to prevent the diffusion of superoxide anions to the anode.

In an initial experiment, the carbon/Pt film surface was coated with a layer of Nafion® and other experimental conditions were kept the same as described above. After a potential (−0.6 V) was applied to the working electrode immersed in the solution, aliquots (0.5 ml) were taken from the reaction media periodically during the reaction and each was added to a Starch-KI aqueous solution (2 ml). In theory, the concentration of the generated hydrogen peroxide in the reaction media should increase with the increase of electrochemical generation time, and accordingly, the amount of iodine complex in the solution will increase, which can be identified visually or by a UV-Vis spectrometer quantitatively. In the present test, the series of aqueous solutions indicated increased formation of hydrogen peroxide with time, and showed that the Nafion® coating prevented the decomposition of hydrogen peroxide on the anode.

The Fabrication of Multilayer Coatings on an ITO Surface:

In the section above, the generation of hydrogen peroxide in an aqueous solution is shown. Next, the generation of hydrogen peroxide in a coating was demonstrated by fabricating a device having a thin layer of hydrogel with a thickness in the range from 50 to 100 microns on the surface of an electrode. The gel layer requires stability to hydrogen peroxide and the reaction condition, good conductivity, and compatibility with the catalyst and electrolytes. A layer-by-layer technique as described above was used to fabricate the gel layer and poly(diallyidimethylammonium chloride) (PDDA), and alginate were used in the fabrication of a multilayer coating.

Substrates of choice for the prototype were glass, silicon or carbon, where the surface of the substrate can be modified with functional groups bearing negative charges such as —$SO_3^{-2}$, —$COO^-$, and —OH and PDDA can be absorbed on the surface through the charge or hydrogen bonding interaction.

After the adsorption of PDDA or polycations on the substrate surface, an alginate layer was absorbed on the surface of PDDA through the charge interaction. Repeating the absorption process alternatively between PDDA and alginate provided a multi-layer on the surface of the substrate and the thickness of the multi-layer can be determined by the numbers of the repeating absorption. A multi-layer with the thickness of 15 PDDA/alginate layers was fabricated on the surface of ITO electrode.

After the multilayer coating was fabricated on the ITO surface, the diffusion rate of oxygen through the multilayer coating was tested by cyclic voltammetry with the scan range from 0.8 to −0.6 v and the scan rate of 60 mV/s in an aqueous solution of sodium sulfate (0.5M, pH of 2) saturated with oxygen. The fact that cyclic voltammograms for ITO electrode remained almost the same with or without the multi-layer on ITO electrode surface suggested that the diffusion rate of oxygen to the surface of the electrode is not affected or slowed by this multi-layer coating.

The ability of a ITO-coated glass electrode having a multi-layer coating of 5 PDDA/alginate layers containing hydroquinone, KI, and starch to generate activated hydrogen peroxide was tested by immersion in a 1% hydrogen peroxide solution for 5 minutes and a dark yellow color associated with iodine appeared in the gel. Initially it was thought that a blue color should appear instead of a yellow one. However, it was realized that the starch was incorporated or locked in the gel and the new conformation of the starch could have prevented the formation of the blue color.

When a potential (−0.6V) was applied to the ITO glass electrode coated with a multi-layer of 5 PDDA/alginate layers containing hydroquinone, KI, and starch immersed in a sodium sulfate aqueous solution (0.5M) with pH of 2 saturated with oxygen, a yellow color appeared in the gel layer after 30 minutes, which showed that electrochemically generated hydrogen peroxide oxidized iodide to provide yellow iodine. Because an ITO glass coated with a thin layer of Nafion was used as the counter electrode in this experiment, the result ruled out the oxidation of migrated iodide on the surface of the anode. This experiment clearly demonstrated that hydrogen peroxide can be electrochemically generated in a hydrogel.

Summary:

In this example, hydrogen peroxide was generated electrochemically in acidic aqueous solution in the presence of hydroquinone or using an electrode containing Pt within 30 minutes. It was also shown that placing a Nafion® coating on the anode reduced the decomposition of the generated hydrogen peroxide at the anode and thus improved the reaction efficiency. Fabrication of the multi-layer coating on an electrode surface was also shown. It was also shown that hydrogen peroxide was generated in response to an electrical signal from an electrode having a multi-layer gel coating.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions by those of ordinary skill in the art without departing from the scope of the invention, it is intended that all matter contained in the above description and shown in the accompanying drawings shall be interpreted as illustrative and not in a limiting sense. In addition it should be understood that aspects of the various embodiments may be interchanged both in whole or in part.

What is claimed is:

1. A coating for a surface, wherein the coating comprises
    a peroxide activating catalyst in an electrically or ionically conductive durable matrix, the durable matrix comprising a polymer layer or a gel where the catalyst is chemically linked to the polymer layer or gel and contains water and/or oxygen; and
    a signal activated peroxide system comprising a positive electrode and a negative electrode which are interconnected by the electrically or ionically conductive durable matrix.

2. The coating according to claim 1, wherein the durable matrix comprises a material that is water insoluble and is sufficiently adherent to the surface to remain on the surface during normal usage.

3. The coating according to claim 1, wherein signal activated peroxide producing system produces hydrogen peroxide.

4. The coating according to claim 1, wherein the system further comprises a positive electrode lead that interconnects the positive electrode with the positive pole of a source of an electrical potential and a negative electrode lead that interconnects the negative electrode with the negative pole of a source of an electrical potential.

5. The coating according to claim 4, further comprising a switch located in the positive electrode lead or the negative electrode lead and which can control whether an electrical potential is applied to the electrodes.

6. The coating according to claim 1, wherein the signal activated peroxide producing system further comprises a mediator which is involved in the transfer of electrons and hydrogen ions to oxygen in the formation of hydrogen peroxide.

7. The coating according to claim 6, wherein the mediator comprises a compound that can be reversibly oxidized and reduced and can transfer hydrogen ions and electrons in a chemical reaction.

8. The coating according to claim 7, wherein the mediator comprises at least one compound that is selected from the group consisting of quinones, anthraquinones, and mixtures thereof.

9. The coating according to claim 1, wherein peroxide activating catalyst comprises at least one compound that is selected from the group consisting of complexes of ethylenediaminetetraacetic acid with metals, EDTA/Fe complexes, tetraaminomacrocyclic ligand complexes with metals, tetraaminomacrocylic ligand/Fe complexes, manganese gluconate, sodium hypochlorite, N-[4-(triethylammoniomethyl)benzoyl]-caprolactam chloride, nonanoyloxybenzene sulfonate, porphyrins, phthalocyanines, ruthenium oxide, indium oxide, and quinones.

10. The coating according to claim 1, wherein the electrode at which hydrogen peroxide formation occurs comprises a material that is selected from metals, platinum, gold, metal oxides, indium tin oxide, conductive metal salts, carbon, carbon/metal composites, intrinsically conductive polymers, materials that include carbon nanotubes, and mixtures of any of these materials.

11. The coating according to claim 2, wherein the coating comprises a gel structure.

12. The coating according to claim 2, wherein the coating is sufficiently permeable to activated hydrogen peroxide to permit the diffusion of activated hydrogen peroxide to a surface of the coating, whereby the activated hydrogen can contact a contaminant that is present on the surface.

13. The coating according to claim 1, comprising:
    a positive electrode and a negative electrode; which are interconnected by
    a water insoluble matrix which is electrically conductive or ionically conductive;
    a mediator that is selected from quinone or anthraquinone and which is present in the matrix or bound to an electrode;
    a peroxide activating catalyst that is selected from EDTA/Fe complex or tetraaminomacrocylic ligand/metal complex; and
    electrode leads for interconnecting the positive electrode and the negative electrode with a source of electrical potential.

* * * * *